(12) United States Patent
Kharraz Tavakol

(10) Patent No.: US 12,079,744 B2
(45) Date of Patent: *Sep. 3, 2024

(54) SYSTEM AND METHOD FOR ACCESSING HEALTHCARE APPOINTMENTS FROM MULTIPLE DISPARATE SOURCES

(71) Applicant: Zocdoc, Inc., New York, NY (US)

(72) Inventor: Oliver D. Kharraz Tavakol, New York, NY (US)

(73) Assignee: Zocdoc, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/228,755

(22) Filed: Aug. 1, 2023

(65) Prior Publication Data

US 2023/0376865 A1    Nov. 23, 2023

Related U.S. Application Data

(63) Continuation of application No. 17/964,189, filed on Oct. 12, 2022, now Pat. No. 11,755,969, which is a
(Continued)

(51) Int. Cl.
*G06Q 10/0631* (2023.01)
*G16H 40/20* (2018.01)

(52) U.S. Cl.
CPC ....... *G06Q 10/06311* (2013.01); *G16H 40/20* (2018.01)

(58) Field of Classification Search
CPC .................. G06Q 50/22; G06Q 10/06311
See application file for complete search history.

(56) References Cited

U.S. PATENT DOCUMENTS

| 2009/0164236 A1* | 6/2009 | Gounares | G16H 40/20 705/2 |
| 2010/0070303 A1* | 3/2010 | Massoumi | G16H 40/20 705/2 |

FOREIGN PATENT DOCUMENTS

WO    WO-2012061339 A1 *   5/2012   ......... G06Q 10/0631

OTHER PUBLICATIONS

"Appointment-Plus Medical Scheduling Software Improving Flu-Shot Vaccination Process at Healthcare Facilities Clinics." PRWeb Newswire Jan. 9, 2013: NA. (Year: 2013).*

* cited by examiner

*Primary Examiner* — Linh Giang Le
(74) *Attorney, Agent, or Firm* — Frank A. Bruno, Esq.; White and Williams, LLP

(57) ABSTRACT

Healthcare appointment information system and method enabling a patient to manage multiple accounts with third party sources through a single account. A user account is created for storing individual user healthcare data such as user preferences (e.g., Monday morning appointments or willingness to be placed on waiting lists), user names and passwords (for accessing third-party sources), contact information (phone, email, text), insurance plans, gender, age, medications, existing appointments and other healthcare information enabling the system to book an appointment on behalf of the patient on one or more availability sources. In addition to booking on the patient's behalf, the account information also enables patient communications with the various sources to be conducted through the system. For example, notifications from other availability sources can be transmitted through the system, which may reformat the message and communicate the reformatted message to the patient. The patient response may then be transmitted via the
(Continued)

system to the source. These communications or their content may also be used to update the user account information.

23 Claims, 15 Drawing Sheets

Related U.S. Application Data continuation of application No. 16/869,747, filed on May 8, 2020, now Pat. No. 11,501,221, which is a continuation of application No. 15/618,629, filed on Jun. 9, 2017, now Pat. No. 10,685,413, which is a continuation of application No. 14/059,957, filed on Oct. 22, 2013, now Pat. No. 9,704,208.

| Common Timeslot Record | |
|---|---|
| Field Name | Description |
| timeslotId | Unique Identifier |
| professionalId | Unique Identifier of the professional |
| remoteSiteId | Unique identifiers of the remote site |
| locationId | Unique identifier of the location where the appointment is available |
| startTime | The start of the available time block for the professional |
| endTime | The end of the available time block for the professional |
| procedureIds[] | An array of the procedures that can be booked during this time block |
| patientTypes[] | An array of the patient types that can be seen during this time block |

FIG. 3

Updating Provider Availabiltiy — 96

| Factor | Value | Refresh Rate |
|---|---|---|
| a) amount of time to appointment | within one week | 5 minutes |
| | one week to four weeks | 10 minutes |
| | more than four weeks | 20 minutes |
| b) popularity of appointment time requested | very popular | 3 minutes |
| | popular | 5 minutes |
| | average | 10 minutes |
| | not popular | 15 minutes |
| c) provider cancellation rate | high | 3 minutes |
| | medium | 10 minutes |
| | low | 20 minutes |

SYSTEM AND METHOD FOR ACCESSING HEALTHCARE APPOINTMENTS FROM MULTIPLE DISPARATE SOURCES

CROSS-REFERENCE TO RELATED APPLICATIONS

This application is a continuation of U.S. patent application Ser. No. 17/964,189, filed Oct. 12, 2022, now U.S. Pat. No. 11,755,969, which is a continuation of U.S. patent application Ser. No. 16/869,747, filed May 8, 2020, now U.S. Pat. No. 11,501,221, which is a continuation of U.S. patent application Ser. No. 15/618,629, filed Jun. 9, 2017, now U.S. Pat. No. 10,685,413, which is a continuation of U.S. patent application Ser. No. 14/059,957, filed Oct. 22, 2013, now U.S. Pat. No. 9,704,208, the contents of which applications are hereby incorporated by reference in their entirety.

FIELD OF THE INVENTION

The present invention relates to a system and method for improved access to and booking of healthcare appointments from multiple disparate platforms and for management of such bookings.

BACKGROUND

Patients now have access to a variety of methods for booking appointments with healthcare providers. Historically a patient would telephone a doctor's office and speak with a receptionist to request the next available appointment. After providing details concerning the reason for the visit, the receptionist would screen the request based on the receptionist's own experience and knowledge of office protocol, provider availability and required resources (e.g., procedure time, required lab tests, examination room and equipment) to determine the next available appointment time. Generally, the patient was given limited options to choose from (e.g., one or two appointment times).

Many patients now have the option to book healthcare appointments online via practice group websites. A practice group may include one or more healthcare providers affiliated with one another and operating from one or more office locations. The appointment booking options and ease of use (user experience) can vary widely on such websites.

Still further, a patient may utilize an aggregator website which offers appointments from a plurality of different unaffiliated practice groups in one centralized booking interface. These aggregator interfaces each have their own search parameters and required patient information for booking appointments.

Despite having multiple options, the patient (user) experience is not always improved. The increase in options has lead to multiple platforms with different booking requirements, formats and procedures that increase the complexity and burden of maintaining up-to-date appointment records and patient information. Many patients have multiple healthcare providers, and those providers may be dispersed across numerous unaffiliated practice groups. If a patient relocates (changes residence), not only does his patient contact information change, but likely all of his provider information changes, as well. If a patient changes jobs, or if his employer adopts a new healthcare plan, the patient's insurance information will change and he will be required to update all of his providers across multiple platforms. Even without changes in residence, employment, or insurance plans, a patient's medical history is a multi-faceted and continually changing data set, e.g., in terms of age, physical condition, medications and injuries. Thus, at any point in time a patient is unlikely to even know what specific information he has provided to any one of his various healthcare providers.

There is thus an ongoing need for improved access to healthcare appointment availability data and for management of patient healthcare data across multiple platforms.

SUMMARY OF THE INVENTION

In accordance with one embodiment of the invention, there is provided a system and method to facilitate patient booking and management of healthcare appointments. The invention provides a greater selection of available appointment times with a greater number of suitable providers, all based on a patient's individual criteria. The patient can maintain his preferred selection criteria at a centralized location and facilitate bookings based on these criteria through a single appointment interface, rather than relying on multiple sources of available appointment data. Further, a patient can easily maintain updated patient information for use across multiple platforms.

In one embodiment the invention provides an interface (e.g., website or mobile application) for accessing healthcare appointment availability across multiple disparate sources (e.g., platforms) for the purpose of scheduling patient visits (appointments) and related tasks. The patient is able to filter availability (across multiple sources) based on his personal criteria, such as accepted insurance plan, location, gender, ratings, hospital affiliations, education, etc. Such filtering across platforms will be based on commonly formatted request parameters, despite the unaffiliated sources (platforms) having disparate filtering criteria, data formats, and/or availability data (e.g., appointment times or other limitations on appointment availability such as type of appointment, length of appointment, office location, etc).

The interface enables a user (e.g., existing or prospective patient) to book appointments from a single source, thus substantially enhancing the user experience. The user is not required to navigate multiple booking sources with different booking requirements. The user's preferred booking requirements are stored in one location and utilized across all booking platforms without requiring entry on each source. In a further embodiment, the user enters and the system maintains the user's up-to-date healthcare information (e.g., appointments, insurance, prescriptions, allergies, etc.) on a single platform. The burden of navigating and maintaining up-to-date healthcare information on multiple platforms is thus removed from the patient (user).

At the same time, the provider is not required to modify their internal (e.g., practice group) procedures. The provider benefits from increased distribution (offering) of its available appointment data across multiple platforms without imposing any significant burden on the provider.

In one embodiment, the invention includes a data ingestion step of searching, crawling and/or parsing multiple sources of available appointment data, e.g., on both aggregated and non-aggregated sources of provider availability, including websites and practice management systems, both internal and external to a practice group. The ingested data may be duplicative, partially overlapping, inconsistent or otherwise not comparable in content or format, and thus requires analysis prior to offering such availability data to users.

In one embodiment, the data ingestion includes importing provider availability from synchronization software located on a remote provider server. In another embodiment, the data is ingested by web crawlers accessing availability data on a provider or aggregator website. In another embodiment, the data is ingested via an application programming interface (API).

In one embodiment, the invention includes mapping (correlating or otherwise transforming) the ingested data into a common format, enabling the system to store and filter the mapped availability data in response to a patient request for booking of an appointment. The mapped data may include required data elements (i.e., required to generate an availability timeslot record) and optional (i.e., not required to generate an availability timeslot record).

In one embodiment, the invention is a booking management platform enabling a patient to manage multiple accounts with third party sources through a single account. A user account is created with the system for storing individual user healthcare data. The account information may include user specific information such as user preferences (e.g., Monday morning appointments or willingness to be placed on waiting lists), user names and passwords (for accessing third-party sources), contact information (phone, email, text), insurance plans, gender, age, medications, existing appointments and other healthcare information enabling the system to book an appointment on behalf of the patient on one or more availability sources. In addition to booking on the patient's behalf, the account information also enables patient communications with the various sources to be conducted through the system. For example, notifications from other availability sources can be transmitted through the system, which may reformat the message and communicate the reformatted message to the patient. The patient response may then be transmitted via the system to the source. These communications or their content may also be used to update the user account information.

Significantly, the account management enables the user (patient) to access all healthcare appointment booking information in one location. The patient is provided with a single calendar of all booked appointments with multiple providers booked on multiple availability sources. The system screens requests to avoid overlapping or competing appointment bookings based on the user calendar. The account avoids or reduces the likelihood of booking an appointment based on obsolete patient information by providing the user with a single location for updating his patient information.

In accordance with one embodiment of the invention, a healthcare appointment availability information system is provided including a processor in electronic communication with a plurality of modules, the modules comprising:
  an ingestion module configured to locate and retrieve healthcare appointment availability data from a plurality of disparate sources via web crawlers and application programming interfaces;
  a transformation module configured to select among overlapping or conflicting ingested availability data for an associated provider retrieved from different sources and map the selected ingested data to common formatted request parameters to identify a particular available healthcare provider appointment;
  a storage module configured to store the ingested or mapped data, and to store user specific account information including user preferences and user access information for accessing one or more of the sources as the user;
  a filtering module for filtering the mapped data based on a user search or booking request and on the associated user account information to determine available appointment times that best satisfy the user search or booking request;
  an interface module for generating an electronic interactive user interface for receiving user search and booking requests for an available provider appointment based on the request parameters and displaying the filtered appointment times based on the user requests; and
  a booking module for booking on behalf of the user, a user selected particular available healthcare provider appointment with the respective source, utilizing the user access information to access the respective source as the user.

In one embodiment, the transformation module is configured to select by assigning a priority among different sources of overlapping or conflicting ingested availability data for an associated provider and selecting from among the ingested data based on the assigned priority.

In one embodiment, the transformation module is configured to map the selected ingested data to a common time slot record for storage in the storage module, the time slot record including an associated provider, appointment location, start time, and end time.

In one embodiment, the common time slot record further includes one or more of procedure type and patient type for the associated appointment.

In one embodiment, the stored user account information includes a user identifier, a source identifier and user credentials to access the respective source as the user.

In one embodiment, the system further includes a refresh module in electronic communication with the processor, the refresh module being configured to update the stored ingested or mapped data by triggering the ingestion module to periodically, at regular or variable time intervals, locate and retrieve the availability data from the sources.

In one embodiment, the ingested availability data includes at least one available time block for an associated healthcare provider and office location; the transformation module is configured to extract the available time blocks from the ingested availability data and assign a priority which varies depending on the source of the extracted time block; and the transformation module is further configured to select among overlapping or conflicting extracted time blocks for an associated provider and office location to generate a single unique time block record based on the priority.

In one embodiment, the filtering module is configured to receive a user search request and filter the mapped data based on the user search request to generate a list of available appointment times from the time block records that best satisfy the user search request.

In one embodiment, the user account information includes user specific preferences for healthcare providers, locations or appointment times, and the booking module is configured to utilize at least one of the user preferences for booking an available provider appointment on behalf of the user.

In one embodiment, the ingestion module is configured to locate and retrieve the availability data by searching, crawling or parsing websites that comprise the sources of the availability data.

In one embodiment, the sources comprise multiple websites, practice group servers, practice management servers, appointment scheduling servers, or provider servers.

In one embodiment, the sources include aggregated sources of appointment availability data collected from multiple unaffiliated providers, and unaggregated sources of appointment availability data from one provider or one practice group.

In one embodiment, the system further comprises a user-source communications module in electronic communication with the processor, the communications module configured for processing, on behalf of the user, user addressed electronic communications from the source.

In one embodiment, the communications module maps an electronic address of the user and an electronic address of the system.

In one embodiment, the refresh module is configured to process one or more factors specific to the appointment time, provider, location or source, to determine the update time intervals.

In one embodiment, the factors include one or more of:
relative amount of time to appointment;
relative popularity of appointment day or appointment time;
relative popularity of provider based on user selection;
relative rate of cancellations or rebookings by provider;
relative process time to retrieve availability data by source; and
search parameter for retrieving ingested data from source.

In one embodiment, the ingestion module is configured to retrieve provider profile data from a source, compare the retrieved provider profile data to existing provider profile data stored on the storage module, and generate profile category specific requests to the source to retrieve category specific profile data.

In accordance with another embodiment of the invention, a computer-implemented method is provided comprising:
ingesting healthcare provider appointment availability data via web crawlers and application programming interfaces from multiple appointment availability sources;
mapping the ingested data to common formatted request parameters for locating a healthcare provider appointment;
storing the ingested data or mapped data on a storage system;
providing an interactive electronic user interface for entry of a user search request correlating to one or more of the common formatted request parameters;
receiving from the interface the user search request;
filtering the mapped data based on the user search request to determine a set of available appointment times that best satisfy the user search request;
providing the set of available appointment times via the user interface for entry of a user booking request for a selected one of the available appointment times;
receiving from the interface the user booking request;
booking on behalf of the user, by accessing the respective source as the user, the selected appointment time and notifying the user of the booked appointment time.

In one embodiment, the method includes:
storing user-specific account information on the storage system, wherein the user-specific information includes user-specific preferences for healthcare providers or appointment times, and one or more of the filtering and booking steps utilizes at least one of the user-specific preferences for filtering or booking on behalf of the user.

In one embodiment, the user account information includes user specific security information for accessing at least one appointment availability source as the user.

In one embodiment, the method includes:
synchronizing the mapped data with the multiple sources by periodically, at regular or variable time intervals, ingesting and mapping the ingested data.

In on embodiment, the multiple sources include: practice management systems and appointment schedulers accessible via application programming interfaces, and websites.

In one embodiment, the method includes determining an expiration time for the mapped data based on one or more of an amount of time prior to an appointment time, an appointment location, and an amount of available appointment times for a provider.

In one embodiment, the ingesting via web crawlers comprises initiating requests based on one or more of: provider location zip codes, provider accepted insurance plans, provider specialties or procedures, provider profile data for a designated provider, and available appointment times for a designated provider.

In one embodiment, a non-transitory computer-readable medium is provided containing instructions to control a processor to perform the steps of the previously described methods.

These and other features of the present invention will be more particularly described in conjunction with the following detailed description and drawings.

BRIEF DESCRIPTION OF THE DRAWINGS

FIG. 3 illustrates one embodiment of a data structure for a common time slot record according to one embodiment of the invention;

FIG. 6 illustrates rules (logic) for determining a refresh rate for updating provider availability according to one embodiment of the invention;

FIG. 8 illustrates a website comprising a remote source of availability data that allows booking an appointment on behalf of a user according to one embodiment of the invention;

FIG. 9 is one example of an electronic interactive user interface provided by the system for entering, searching and booking requests according to one embodiment of the invention;

DETAILED DESCRIPTION

Figure 1:
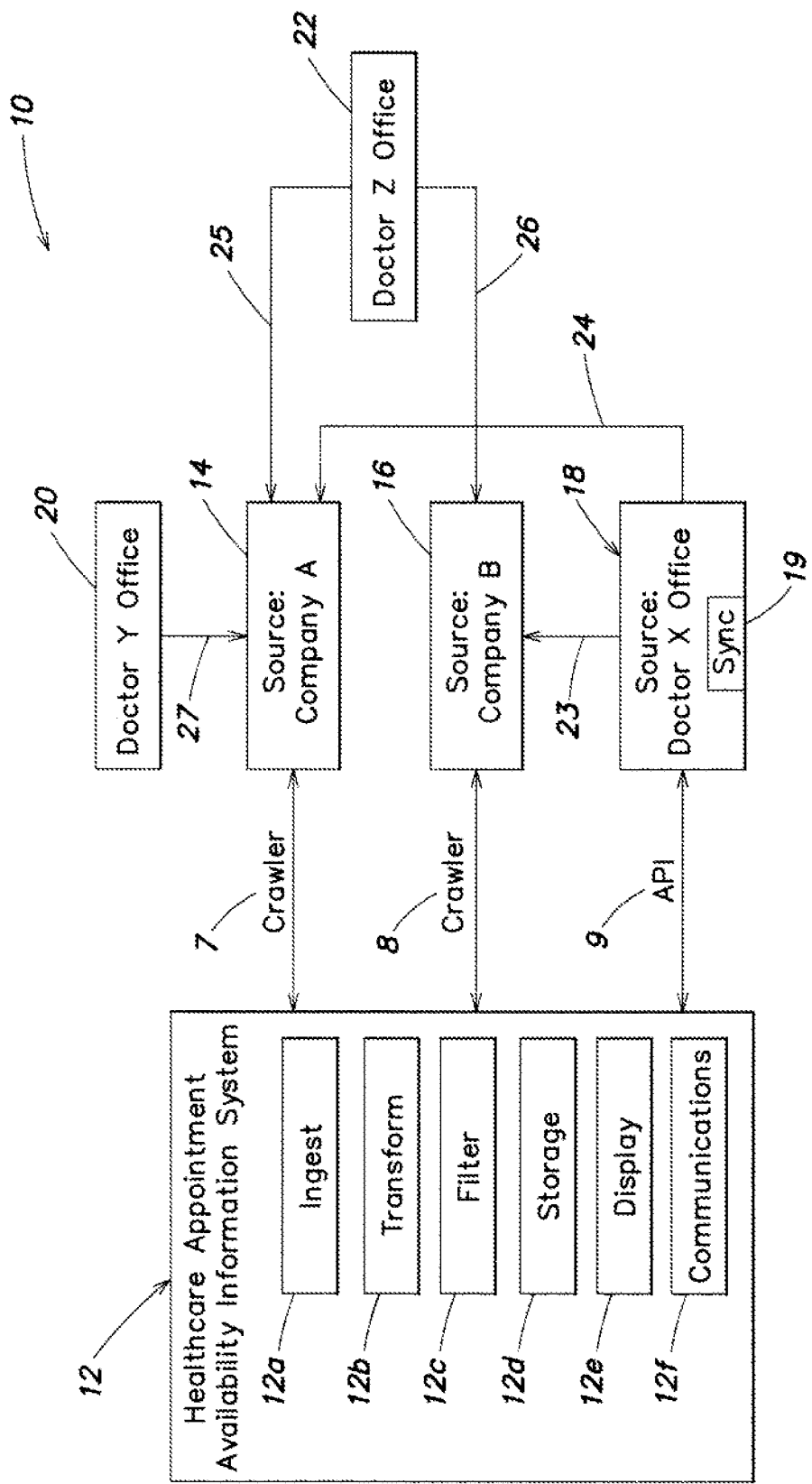
FIG. 1 is a schematic diagram of a healthcare appointment availability information system according to one embodiment of the invention, shown communicating with multiple sources of availability data.

Various embodiments of the present invention are now described with reference to the drawings. In the following description, for purposes of explanation, numerous specific details are set forth in order to provide a thorough understanding of one or more implementations of the present invention. It will be evident, however, that the present invention may be practiced without these specific details. In other instances, well-known structures and devices are shown in block diagram form in order to facilitate describing the present invention.

As used in this application, the terms "component", "system" or "module" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

The present invention may also be illustrated as a flow chart of a process of the invention. While, for the purposes of simplicity of explanation, the one or more methodologies shown in the form of a flow chart are described as a series of acts, it is to be understood and appreciated that the present invention is not limited by the order of acts, as some acts may, in accordance with the present invention, occur in a different order and/or concurrent with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

As used herein, the term "provider" includes a physician, doctor or other medical professional (nurse, physician assistant) administering patient care, as well as members of his/her staff that assist in providing such care or are responsible for maintaining the provider's scheduling calendar, patient records, billing, insurance, prescription and other services.

A "practice group" or "provider group" may be any entity linking a group of providers through shared facilities, services or referral agreements. This may include, but should not be limited to, one or more hospitals, clinics, pharmacies, insurance networks, medical groups and multi-doctor practices.

A "user" of the system described herein may be a patient or an entity acting on behalf of the patient; a "patient" means an existing patient, or a prospective (potential new) patient, of a provider or practice group.

As used herein, a "source" provides a network-based service to patients and to one or more providers, practice groups (e.g., physician groups, hospitals, clinics) and/or insurance providers that publishes healthcare provider availability data. For example, a source may provide an application or web-based data processing service (e.g., for online appointment booking and patient communications) and interface to a computer, server, or other wired or wireless mobile communications device (e.g., cell phone, tablet computer, etc.) of one or more patients, providers, practice groups, and/or insurance providers.

a) Ingesting and Mapping Provider Availability Data

Figure 2:
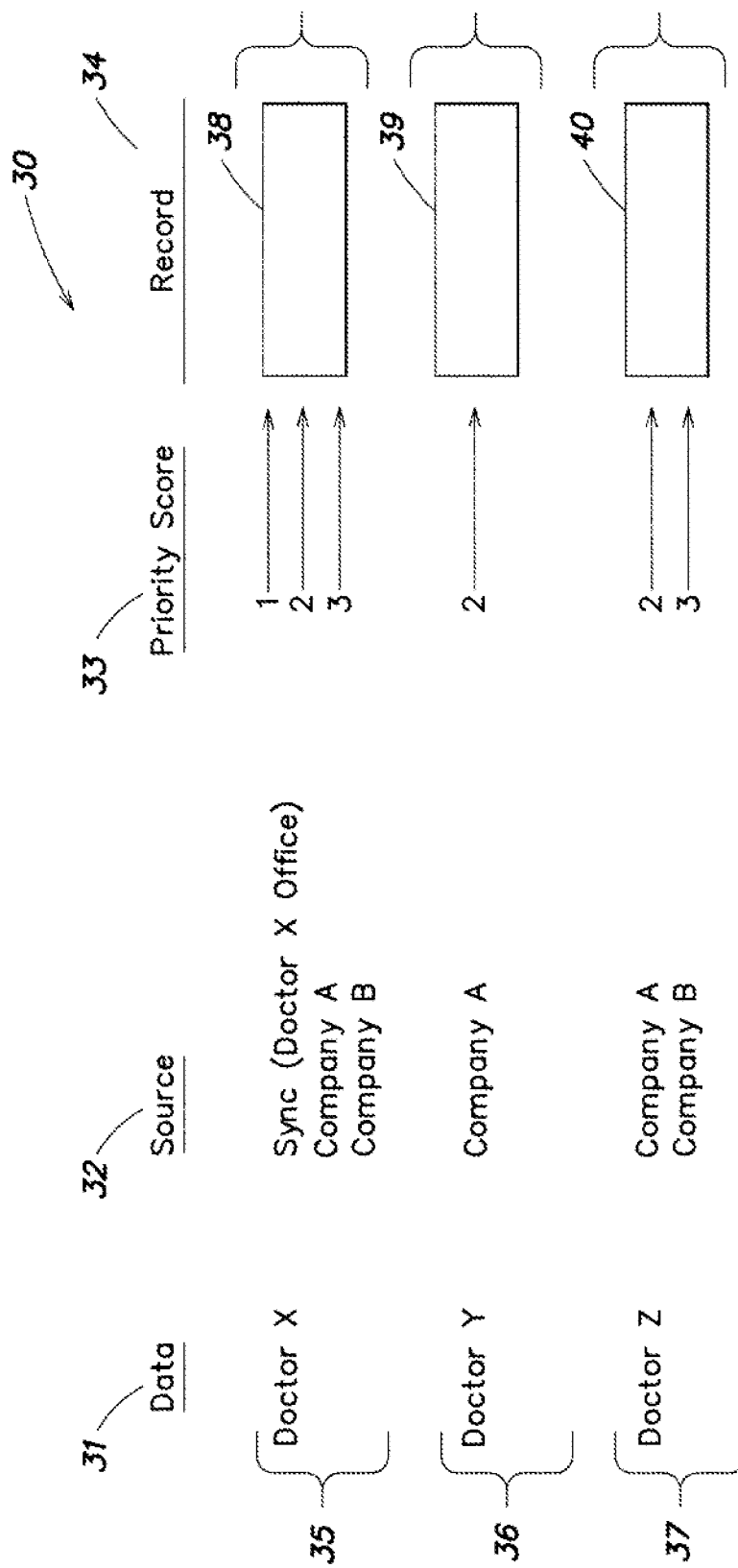
FIG. 2 is a schematic diagram of a method of generating a unique appointment availability record from overlapping or inconsistent data received from multiple sources.

FIGS. 1-2 illustrate one embodiment of a system and method for facilitating patient access to, booking and management of healthcare appointments. In FIG. 1 a healthcare appointment availability information system 10 comprises a server 12 that ingests available appointment data via a web crawler 7, 8 or API 9 from multiple unaffiliated sources 14, 16, 18, here identified as Company A, Company B, and Doctor X office respectively. Each source may be an aggregated source of appointment availability data from multiple unaffiliated providers (e.g., Company A), or an unaggregated source of doctor availability data from one provider or one practice group (e.g., Doctor X office). In this example, Doctor X office provides its doctor availability data to both Company A and Company B via network connections 23, 24. Doctor X office also supplies doctor availability data directly to system 12 via network connection 9; in this example, synchronization (Sync) software 19 located at Doctor X office server transmits data via an API to server 12. The synchronization software 19 may pull the doctor availability data from Doctor X office's scheduling software or practice management software (which may be an internal or external service to Doctor X office). Further, Doctor Z office 22 sends its doctor availability data via network connections 25, 26 to Company A and Company B respectively. Doctor Y office 20 supplies its doctor availability data via network connection 27 to Company A. Thus, in this example system 12 receives (ingests) doctor availability data directly from Doctor X office 18 (referred to as a "primary source") and receives doctor availability data originating from Doctor X office and Doctor Z office indirectly via Company B's website 16 (referred to as a "secondary source"). Server 12 also receives doctor availability data originating from Doctor X, Doctor Y and Doctor Z offices indirectly via Company A's website 14. In other embodiments, Company A or B may also provide API's to the system, and the Doctor X connection could be other than an API.

The server 12 includes processing and storage modules that receive 12a the ingested data and transform 12b the ingested data into a common format that can be searched by the system filters 12c. For example, the ingested data from different sources may include multiple copies of identical data for a specific appointment, similar but different data for a specific appointment, or incomplete data for a specific appointment. The data transformation resolves discrepancies and generates unique (non-duplicate) appointment data records 34 (see FIG. 2) that can be filtered by common formatted parameters, and then stores the mapped (transformed) data records 34 on a storage system 12d. Thus, when a system user (patient) requests a search for available appointment times according to the user's specified criteria, the system already holds (stores) a plurality of records in a common format that can be searched (filtered) for responding to the user's search request. In another embodiment, the raw ingested data is transformed and filtered on the fly (at the time of the user request, rather than filtering previously transformed and stored data).

FIG. 2 illustrates one method 30 of mapping (transforming) the ingested data, wherein different priority scores 33 are assigned to data elements ingested from different sources 32. Typically the score is used to determine and select the most reliable data for inclusion in record 34 (e.g., a database record). For example, first row 35 contains ingested data for a single or overlapping available time block for Doctor X that has been received by system 12 from three sources: the Sync software 19 from Doctor X office 18, and also from web crawlers 7, 8 collecting Doctor X data from Company A website 14 and Company B website 16, respectively. Each data source is assigned a priority score. In this example, the lowest priority score (number) prevails, which for Doctor X is the data from Sync software 19 received directly from Doctor X office 18 (primary source). A single record 38 for a unique appointment time block is generated for the Doctor X data ingested from the multiple sources and may comprise, depending upon the algorithm for transforming the ingested data, only the data received from Sync 19, or some combination of data from Sync 19, Company A and/or Company B.

As illustrated in the second row 36, server 12 received Doctor Y appointment time data from one source, Company A. Company A has a priority score of 2 and in this case, being the only source (lowest priority), this data is used to create a single record 39 for a unique available appointment time block for Doctor Y.

As illustrated in the third row 37, server 12 received available appointment time data for Doctor Z from both Company A and Company B, assigned priorities of 2 and 3 respectively. Again, depending on the algorithm, the ingested data is transformed to a single record 40 for a unique appointment time block for Doctor Z.

This is just one example of a system and method for ingesting and mapping provider availability data from multiple sources into a common format for storing and filtering. It will be apparent to the skilled person that various other methods can be used for ingesting, transforming and storing the doctor availability data from multiple sources.

b) Common Timeslot Record

FIG. 3 illustrates one embodiment of a data structure 50 for a common timeslot record (e.g., the record 34 of FIG. 2). Each record includes a timeslotId 51, which is a unique identifier for the time block. As used herein, a time block is a continuous period of time, of variable size, which may accommodate one or multiple office appointment times depending upon the reason for the visit (e.g., procedure to be performed) or other basis for determining appointment time as designated by the provider. Preferably, the system stores provider-specific data for each provider, which may include the provider's individual designation of appointment times for different procedures; if no procedure time is designated by the provider, a default procedure time may be utilized. Again this is just one embodiment and the present invention is not so limited; other methods and data structures for generating and storing appointment availability time can be utilized.

The timeslot record further includes a professionalId 52, which is a unique identifier of the healthcare provider (having the associated available time block). The next field, entitled remoteSiteId 53, is a unique identifier of the source of availability data contained in the record. The next field, locationId 54, is a unique identifier of the geographic location of the provider office for the appointment at the time identified in the record. The next field, startTime 55, is the start of the available time block for an office appointment with the designated provider. The next field, endTime 56, is the end of the available time block for the designated provider. The next field, procedureIds[ ] 57, is an array of the procedures that can be booked during this time block (e.g., as allowed by the associated provider). The next field, patientTypes[ ] 58, is an array of the patient types that can be seen during this time block.

In one example, a time block record as illustrated in FIG. 3 identifies one unique time block for a provider Dr. Smith (professionalId), the available appointment time slot having been ingested from Dr. Smith's practice group website (remoteSiteId), and identifies Dr. Smith's New York City Office address (locationId) where the appointment will occur. The record designates the start of the time block as 1:00 PM (startTime), and the end of the time block is 3:00 PM (endTime). The allowed procedures during this time block (procedureIds[ ]) include an annual physical, flu shot, and referral request. The time block may allow for booking of multiple appointments (e.g., a first appointment from 1-2 PM and a second appointment from 2-3 PM). The patient types (patientTypes[ ]) that can book during this appointment time block with Dr. Smith include only existing patients (excludes new patients), only male patients, and only adults over the age of 18.

In the illustrated embodiment, one or more database tables contain unique identifiers for each time block, provider and booked appointment that can used to uniquely associate one to another.

c) Search Filters

Figure 4:
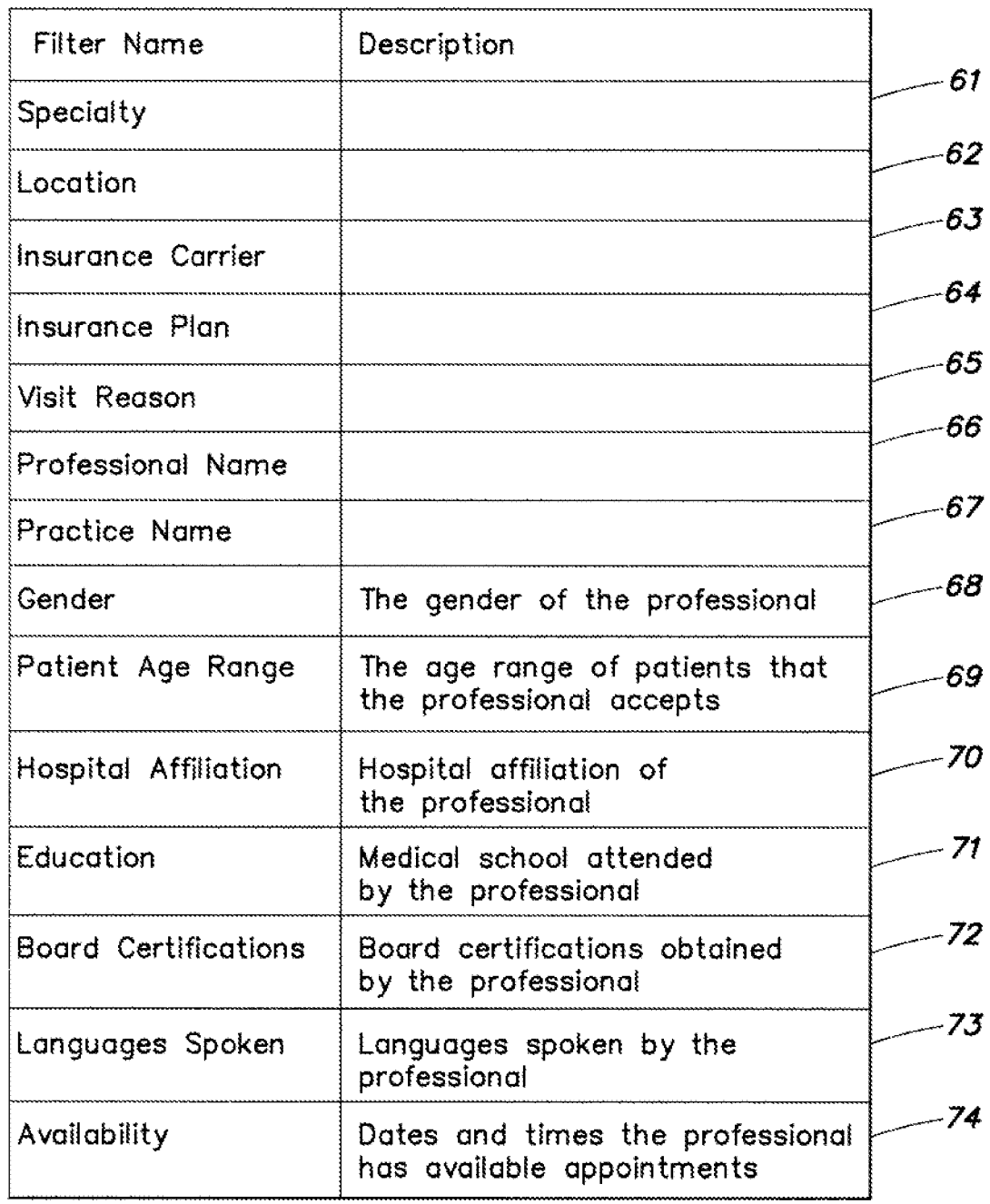
FIG. 4 illustrates a set of search filters for filtering the ingested and transformed availability data according to one embodiment of the invention.

FIG. 4 illustrates one embodiment of a set of search filters 60 for filtering the mapped data stored on system 10 to determine available appointment times that are applicable (responsive) to a user's search request. The system 10 includes a user interface module (e.g., 150 as shown FIG. 7) that provides an interactive electronic interface (e.g., website) displaying allowable search parameters (e.g., provider specialty, office location, reasons for visit) that enable entry by the user of a user search request comprising one or more of the allowable search parameters with user selected restraints. The interface (website) receives and processes the user's search request, filtering the stored (mapped) data (records 34) for available appointment times responsive to the request, and then publishes the available appointment times on the user interface for selection by the user of one of the available appointment times. The system then books the selected appointment time with the associated provider on the source from which the mapped data was obtained, and the system communicates confirmation of the booked appointment to the user (e.g., via the interface or other electronic communication means such as email or text message).

A search module, a booking module and an interface module for implementing one embodiment of the invention are described further below with regard to FIG. 7.

FIG. 4 illustrates one example of a set of search filters for filtering the system's stored availability data in response to a user's search request. The filter names (search parameters) are generally indicative of the function/description and include, for a given provider, one or more: Specialty 61; Location 62; Insurance Carrier 63 and Insurance Plan 64 (accepted by the provider); Visit Reason 65 (which the provider has designated as appropriate); Professional Name 66 (of the provider) and Practice Name 67 (of provider's practice group); Gender 68 (of the professional); Patient Age Range 69 (of patients that the professional accepts); Hospital Affiliation 70; Education 71 (including medical school); Board Certifications 72; Languages Spoken 73; and availability 74 (the dates and times the professional has available appointments). This is just one example of possible search filters and is not meant to be limiting.

d) User Account Management

Figures 5A, 5B:
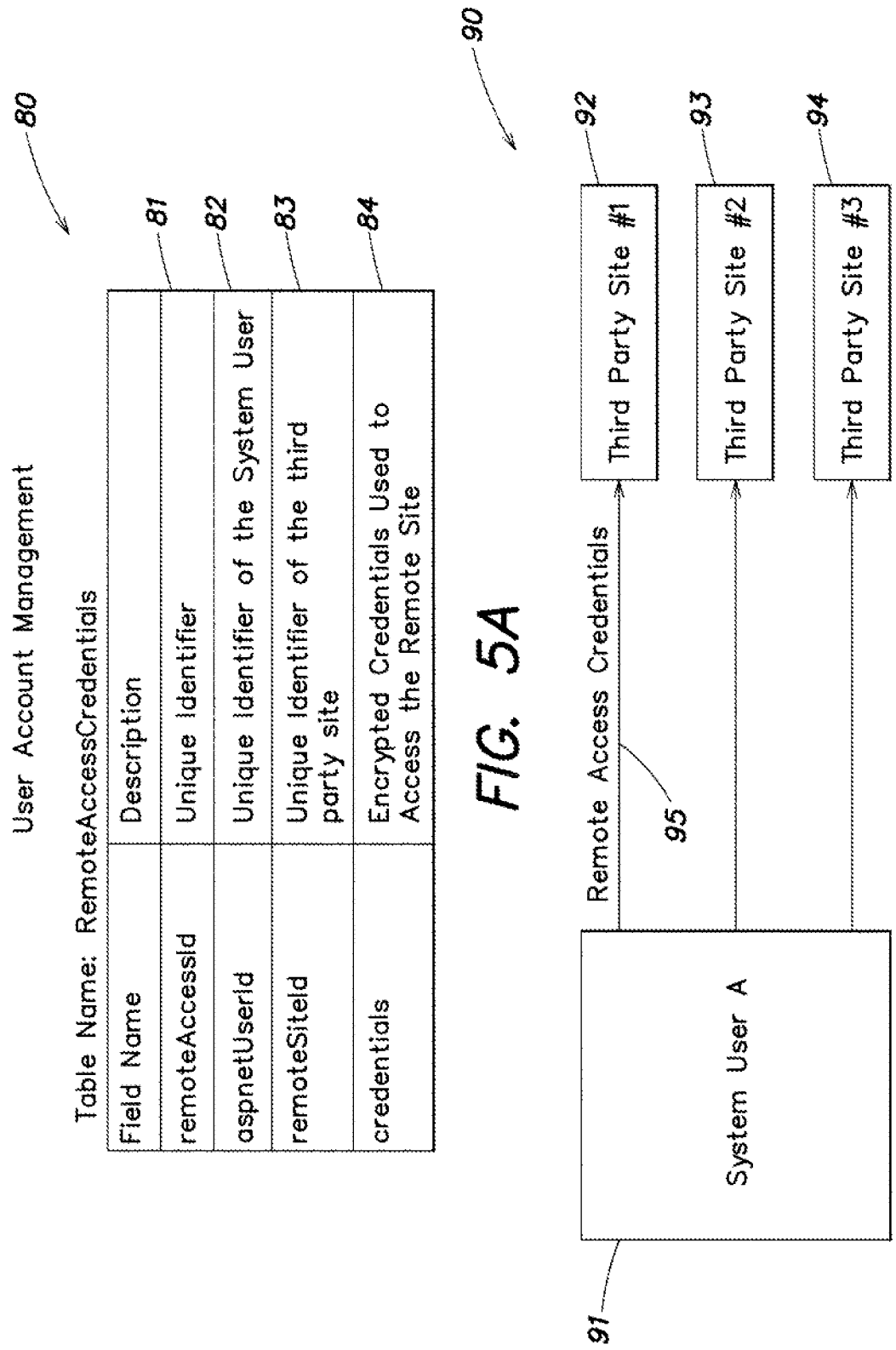
FIG. 5A illustrates a data structure for user account information including user credentials for accessing a remote third party site.
FIG. 5B is a block diagram illustrating a method of accessing one or more remote third party sites utilizing the user's remote access credentials.

FIGS. 5A-5B illustrate one embodiment of user specific information collected and stored by server 12 to enable booking of an appointment on behalf of a user on a remote third party site. In another embodiment, the user specific information may further include user preferences for booking healthcare appointments, for example, provider preferences (e.g., based on education, gender, age) or user preferences regarding appointment times (e.g., particular days of the week or time of day).

FIG. 5A illustrates one example of a data structure for storing remote access credentials of the user, here a database table 80 named "RemoteAccessCredentials" with four fields. A first field, labeled remoteAccessId 81, is a unique identifier of the access record. A next field, labeled aspnetUserId 82, is a unique identifier of the user. A next field, labeled remoteSiteId 83, is a unique identifier of the source, namely the third party server or website on which the associated appointment can be booked. A next field, labeled credentials 84, contains the user's credential information (e.g., password and user name, in encrypted form) that can be used to access the remote site.

FIG. 5B further illustrates a method 90 whereby the server 12 accesses (via electronic communication channels 95) one or more remote sites 92-94 to book an appointment on behalf of a user. Here a specific user A, has a user account 91 which includes his user access credentials for three different third party sites 92, 93, 94. The system utilizes these credentials at the respective sites to book or otherwise communicate with the site on behalf of the user. Thus, the system not only provides a booking platform with a greater range of available appointment times for selection by the user, but also enables booking of multiple appointments on behalf of the user on these different sites which greatly reduces and simplifies (from the user's perspective) the management and booking of all the user's healthcare appointments.

Again, this example is a non-limiting example. Additional user account information can be utilized by the system to further individualize the search and booking requests on behalf of a given user and maintain at a single location, up-to-date healthcare appointment information of that user.

e) Updating Provider Availability Data

In one embodiment of the invention, a method is provided for updating the appointment availability information wherein the update time interval varies with the nature of the data collected as well as the nature of the source providing the data. The available time data is likely the most important data to be refreshed, however, other data, such as provider profile (e.g., specialties, hospital affiliations, accepted insurance plans) and other provider-specific appointment information (e.g., different minimum appointment times designated for each reason for visit) may also be refreshed, likely on a different (less-frequent) schedule.

In one example, the time block data of FIG. 3 is refreshed based on one or more factors, wherein each factor may include multiple categories with different refresh rates. FIG. 6 illustrates one example of a rules set (logic) 96 for determining a refresh rate (time interval). In this example, three factors 97-99 are defined, each having a different set of values, and each value having a different refresh time. The first factor 97, amount of time to appointment, is one factor that may influence the rate at which the available time blocks change (e.g., are booked, cancelled or rebooked). In this example, for a shorter amount of time to appointment, e.g., within one week, the refresh rate is assigned a 5 minute interval; for an intermediate amount of time, one week to four weeks, the refresh rate is 10 minutes; and for a longer amount of time, more than four weeks, the refresh rate is 20 minutes. This reflects a finding that near-term appointments change more frequently. The system may monitor and adjust the applicable factors, values and refresh times based on observed (monitored) performance, such as the number of near-term booking requests that are denied due to prior booking.

A second factor 98 is the popularity of appointment time requested. A very popular appointment time (e.g., first appointment of the day) is given a more frequent refresh rate of 3 minutes; a popular time is given a refresh time of 5 minutes; an average popularity appointment time is assigned a refresh rate of 10 minutes; and a not very popular time is given a refresh time of 15 minutes.

A third factor 99 is the provider cancellation rate. For example, a provider may have (based on prior monitoring) a relatively higher rate of cancellations (and rebookings) than other providers. If so, the higher number of rescheduled appointments means the available time blocks change more rapidly and thus should be refreshed more often.

In this example, if no value is assigned to a particular factor, a default value, such as a 5 minute refresh rate may be used.

In one example, all of the relevant factors may be utilized and weighted (each factor assigned a relative weight value) to determine a desired refresh rate. In another embodiment, the method selects the lowest minimum refresh time from among the relevant factors and values. The refresh rates may be adjusted over time as the system learns from experience an optimized refresh rate for a given provider or source, e.g., based on the number of ingested and attempted bookings that are then rejected by the provider or source as already filled due to a change in the provider's schedule.

The system can also take account of the processing burden of the refresh method or limitations of the source. Typically, a company (source) providing a practice management scheduling service for multiple practice groups will have a well-defined API based on its existing partnership with the multiple practice groups, e.g., enabling requests specific to individual doctors and individual time periods (e.g., a week, day or month). This API will allow the server 12 to submit focused ingestion requests (by provider or time period) that will reduce the processing time, and may thus allow for more frequent updates.

If the source does not have a well-defined API, then each refresh event will likely require more time and more processing. In one example, the ingesting method may select specific web pages (URL's) that provide the most relevant data, parse all data on those pages, and then map the ingested data into the system's common format.

Again, alternative embodiments will be apparent to the skilled person and are included in the present invention.

f) Appointment Availability Information System

Figure 7:
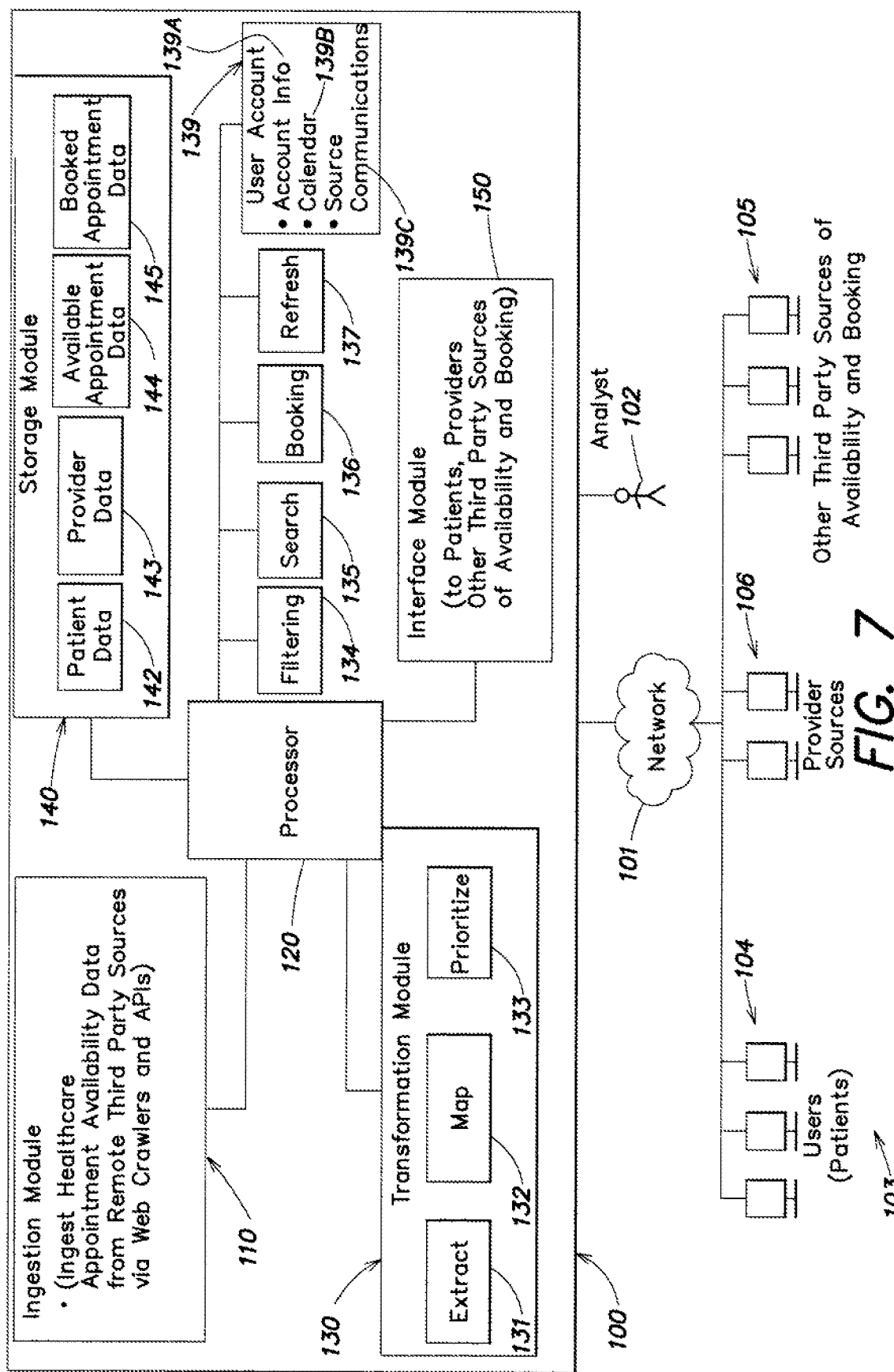
FIG. 7 is a more detailed schematic diagram according to one embodiment of the invention.

FIG. 7 is a more detailed illustration of a healthcare appointment availability information system 100 in accordance with one embodiment of the present invention. The system is implemented to aggregate, analyze, store and publish healthcare appointment availability information from multiple platforms and to book appointments on the user's (patient's) behalf on the multiple platforms. The users of the system do not need to spend hours searching for and navigating through multiple sources (platforms) of appointment times.

The system is provided with a processor 120 which is adapted to control and facilitate the functions of various modules and sub-modules of the system as described below. The system may be implemented with any type of hardware and software, and may be a pre-programmed general purpose computing device, such as a server, a personal computer, a portable computer, a hand-held device, a wireless device, or any such combination of devices. The system may be a single device at a single location or multiple devices at one or more locations that are connected together using any appropriate communication protocols over any communication medium, such as electric cable, fiber optic cable, or in a wireless manner (using radio frequency or other technologies).

The modules described herein as performing a particular function can be implemented in any hardware, software, or a combination thereof, and two or more modules can be combined, or a single module divided, in various embodiments of the invention.

The healthcare appointment availability information system 100 is connected to a network 101 that allows remote access from and to the system so that healthcare appointment availability information can be retrieved and published, to allow bookings at remote sites, and to process user-source communications. The network allows the system 100 or administrators thereof, such as analyst 102, to access the remote sources 105-106 which include both aggregated sources of healthcare appointment availability information, and primary sources of healthcare appointment availability information. In this example, a primary source 106 is typically specific to and originating from the provider himself, or his practice group. An aggregated source 105 may provide availability information collected from multiple providers across multiple practice groups. The sources include but are not limited to a provider server, a practice group server, a provider website, a practice group website, a hospital website, an insurance company website, and a practice management service website. In addition, the network 101 allows users 103 to access the system 100 and obtain information provided thereby via a terminal 104. The terminal can be implemented in any manner, for example, as a personal computer, a portable computer, a handheld device, a wireless device, etc.

The network 101 may be any type of communications channel, such as a local area network, a wide area network such as the Internet, and direct computer connections, and may be accomplished in any wired or wireless manner using various technologies and various communication hardware and protocols.

In the illustrated embodiment, the system 100 uses various modules that access and utilize the processing power of the processor 120 to perform various functions. The system 100 includes an interface module 150 that allows an analyst or other authorized individuals to interface with the system 100 to initiate various functions as described and to maintain the system 100. The interface module 150 provides a navigation interface which allows users to retrieve, select and book available healthcare appointment times provided by the system 100 as described herein.

The healthcare appointment availability system 100 also includes an ingestion module 110 that functions to locate and retrieve (ingest) healthcare appointment availability information from various sources e.g., 105, 106. The ingestion module may include various sub-modules for ingesting available time block data, and provider data from the various sources.

The system 100 also includes a transformation module 130 that functions to extract 131 various data elements from the ingested data, as well as various meta-data. In this example, the transformation module includes a mapping sub-module 132, e.g., for mapping the extracted data to a common format, prior to storing on the storage module 140. A prioritizing or selection sub-module 133 implements a set of rules (logic) for selecting among conflicting ingested data (see FIG. 2 above). A filtering module 134 processes user search requests (received and processed by search module 135) by filtering the stored available appointment data and/or provider data stored on the storage module 140. The filtering produces a set of available appointment times that best satisfy the user's search request parameters. These appointment times are published via interface module 150 for review and selection by the user 103 of a desired published appointment time. A booking module 136 receives and processes the user's booking request to schedule an appointment at the selected appointment time, by booking the requested appointment time with the source on behalf of the user. A user account module 139 processes and stores user account information 139A, a user calendar 139B (e.g., of booked appointments), and user-source communications 139C (that are processed by the system as previously described). The booking module 136 utilizes patient data 142 (which includes the user account information previously described) and available appointment data 144 stored in the storage module 140 to accomplish the booking and stores the booked appointment data on storage sub-module 145. A calendar sub-module 139B receives booked appointment data from storage module 145 for generating a user-specific calendar of the user's booked appointments and other user (patient) data from storage sub-module 142. The calendar sub-module 139B generates a graphical display, typically in a grid or other calendar format, on interface module 150 for review and navigation by user 103 via terminal 104, enabling the user to manage, edit and maintain an updated calendar of booked appointments and other patient data.

The mapping sub-module 132 also receives and processes provider data received from sources 105 and 106, which is also mapped into a common format and stored as provider data 143 on storage module 140. The provider data, which may include accepted insurance plans, office locations, gender, hospital affiliations, etc., can be used by the filtering module 134 along with processing available appointment times in responding to a user's search request.

The ingestion module 110 is adapted to locate and aggregate such information by searching, crawling and/or parsing websites, including both aggregated and non-aggregated sources (e.g., websites or servers) 105, 106, for healthcare provider availability information and other provider information data. The ingestion module 110 is also adapted to access third party sources 105, 106, such as remote servers, via a programming interface to applications residing on the remote server. Such interface may comprise a set of request messages and response messages for sharing content and data between applications, which requests may be customized for a particular source (e.g., to request availability data by specified provider, procedure type, patient type, reason for visit, or appointment time).

Figure 8:
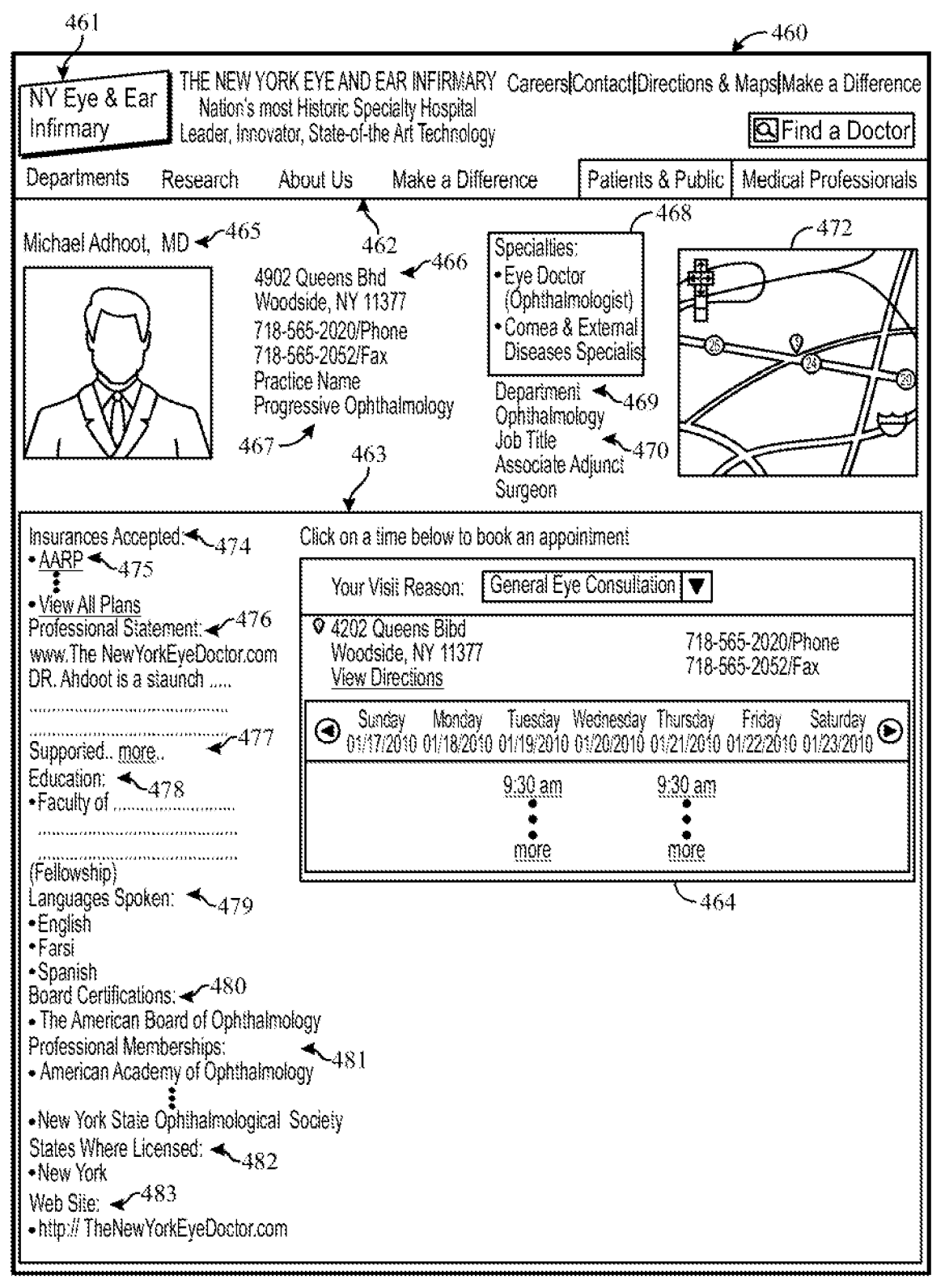

For example, FIG. 8 illustrates one example of a third party website with healthcare provider availability information, and other provider data, that the ingestion module 110 can access (e.g., parse) to collect data for subsequent processing and storage on the system 100. FIG. 8 shows a webpage 460 from an online hospital directory for an affiliated provider. Below the running head 461 are text, photos and graphics describing one individual provider 465 and his provider profile information 466-470. This hospital directory includes a listing 464 of available appointments with the provider for online booking. The profile information includes the provider's name 465, contact information 466, link to the provider's practice group website 467, specialties 468, department 469 and job title 470. Window 472 is a street map identifying one or more locations of the provider's offices. A plurality of headers 474-483 provide additional provider profile information and links to webpages on the same or different sites with additional profile information. The ingestion module 110 collects various data from this webpage and linked webpages as described further below.

The ingestion module 110 can be implemented with a search harvester tool for collecting the available time and provider data. A search harvester refers to any engine program or tool capable of programmatically retrieving information according to input parameters, and processing the search results to ensure that only some particular types of information from the search results is provided as the output. For instance, numerous crawler script engines, search engine results page manipulators, and configurable web crawlers are already known and existing in the art that can be used. Instructions to configure the search harvester tool can be provided by a configurator together with an analyst to input instructions, enabling the harvester to perform a desired function of collecting healthcare appointment availability information. Based on the analyst instructions and configuration of the search harvester for locating and collecting healthcare appointment availability information (which includes provider information), the harvester is preferably implemented to allow automated navigation (controlled, filtered crawling) and automated search methods, to obtain and filter the information, and further perform periodic refreshing.

In one embodiment, query spawning rules and search results validation rules are entered by the analyst 102. The search harvester electronically submits the input to the remote source, for example, to a search engine provided by the source. The information retrieved and processed as results from the source may be a listing of available time files and provider data files that is the output of the ingestion module 110. In various embodiments, the analyst may use a comma delimited file prepared by the analyst or a web-based user interface for entering the rules. Such tools and techniques can be used for the analyst to validate the search results that are known in the art. The constraints defined by the analyst and applied to the ingestion and transformation modules may be textual, or arithmetic, such as defining provider names, insurance plans, data ranges, etc.

The transformation module 130 analyzes the raw data (e.g., the ingested available time and provider data) to produce various files having defined attributes and accompanying metadata. Clustering and related technologies can be employed for eliminating duplicate, overlapping or conflicting items, such as duplicate time entries retrieved from different sources. The processed files are stored in the storage module 140, and can be used to populate the fields of various templates for publishing healthcare appointment availability data on the interface module 150. The interface module 150 in the illustrated implementation provides a website that allows a user to view the generated sets of available appointment data and associated provider data via a terminal 104 connected to a network 101. The interface module may provide a user interface with various selectable links, menu items and the like to facilitate the user's navigation of the website content. For example, if a user clicks on an available appointment time, he may be taken to an appointment summary, which includes more detailed information regarding the desired appointment.

To facilitate the updating process, the system 100 includes an update or refresh module 137 to periodically, at regular or variable time intervals, ingest data from sources 105, 106, or otherwise monitor the content of sources 105, 106. In one embodiment, an event (e.g., differential data since the previous update) triggers a request to refresh or to modify the refresh rate. The results of such monitoring can be sent to the analyst, for example in an email, with a message to the analyst suggesting a new refresh rate or that modification of the refresh algorithm be considered or entered into the system for future use.

Figure 9:
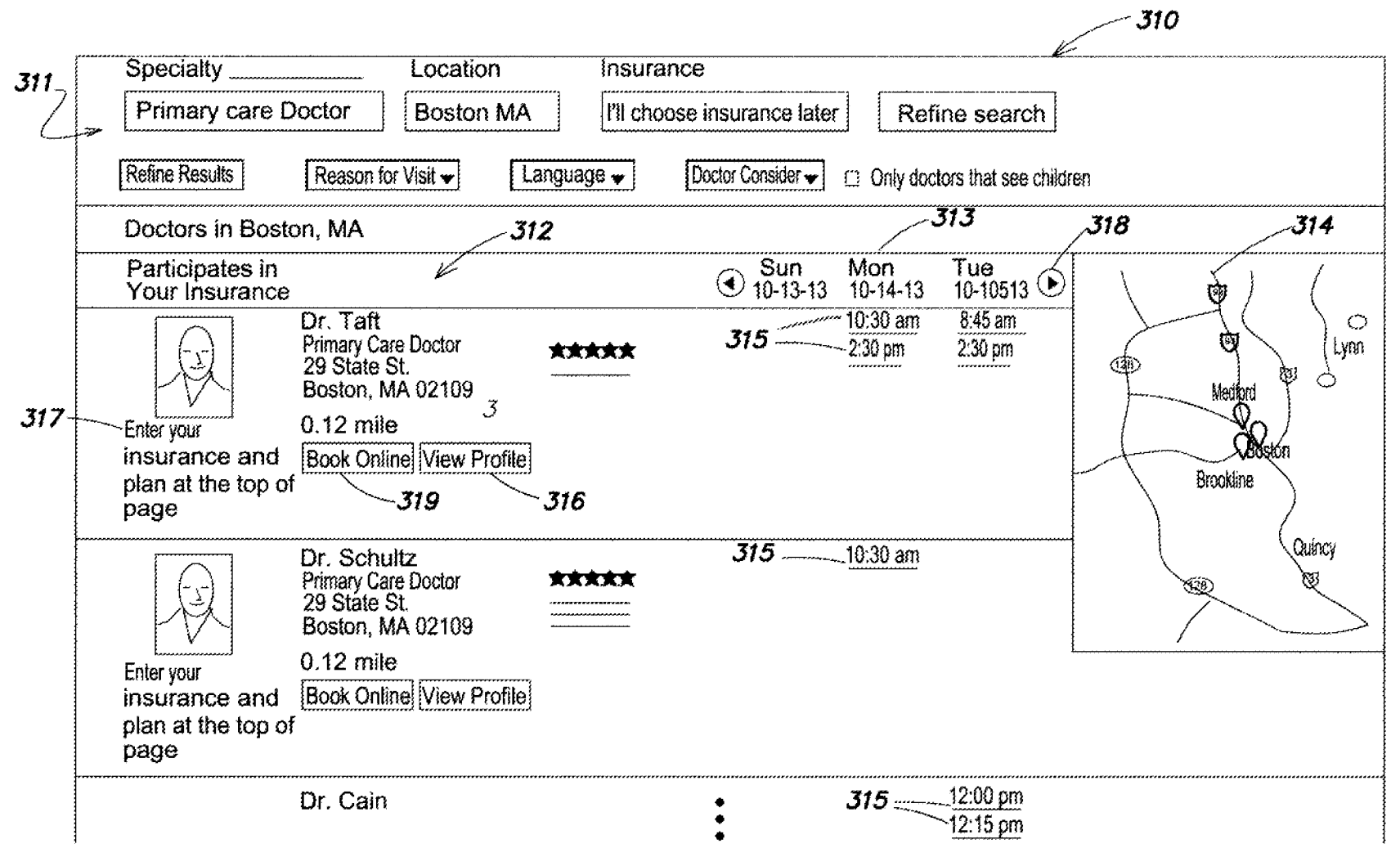

FIG. 9 illustrates a webpage 310 (interactive user interface) for entering search requests and displaying search results in response to a user input search criteria 312. Windows with pull-down menus enable user selection of search parameters, here by specialty, location, and insurance. Below the search parameters is a display, here in row/column (grid) format, that identifies providers 312 having available appointment times 313 meeting the search criteria. The next three days are sequentially displayed across the page, with available appointment starting time slots 315 listed below the relevant day and aligned with the respective provider. The webpage also includes a map 314 with markers identifying the location of the provider's office for the associated available appointment time; a link 316 to request more information regarding the provider (view provider profile); and a link 317 to determine whether a provider would be considered within the network of the patient's insurance plan. The patient can select a time slot link 315 to book an appointment at the designated start time, by simply clicking on the link or hit the Book Online button 319. In addition, the patient is provided with a link (arrow 318) to view additional appointment times that are available in the future, such as the next week. This is just one example of a means by which interface module 150 publishes the available appointment times and available information for search and booking by the user 103 on terminal 104.

g) Method Embodiments (Ingesting, Mapping, Filtering, Publishing, Booking)

Figure 10:
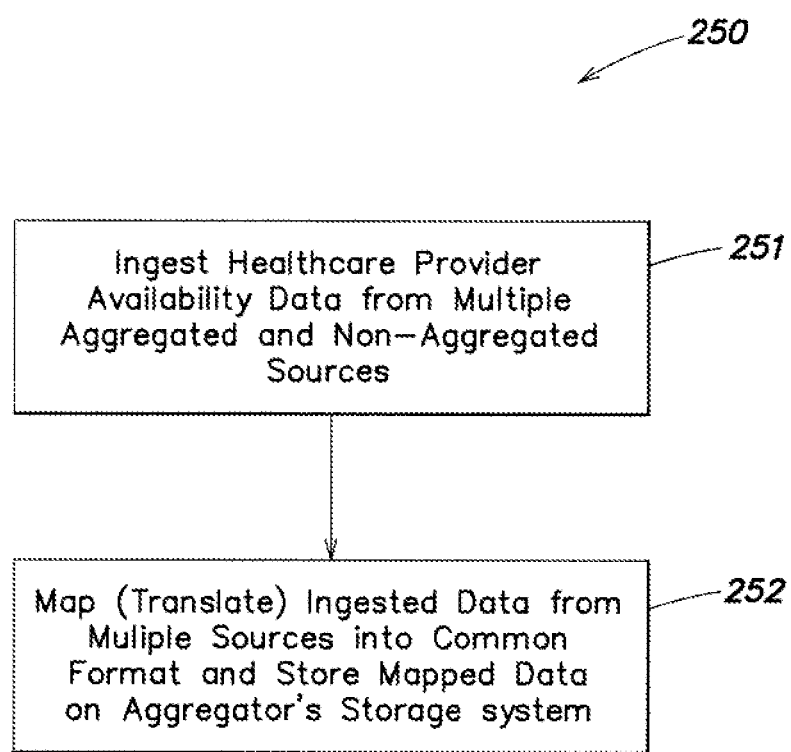
FIG. 10 is a flow chart illustrating a method of ingesting and transforming ingested data according to one embodiment of the invention.

FIG. 10 is a flow chart illustrating a first method embodiment 250 of the invention, which may be implemented as previously described (FIGS. 1-2). In a first step 251, healthcare provider availability data is ingested from multiple aggregated or non-aggregated sources (e.g., via web crawlers and APIs). In a next step 252, the ingested data from the multiple sources is mapped (transformed) to common formatted parameters and the mapped data is stored on the storage system. The mapping step may include generating a single unique data record based on, for example, a priority score of the respective source.

Figure 11:
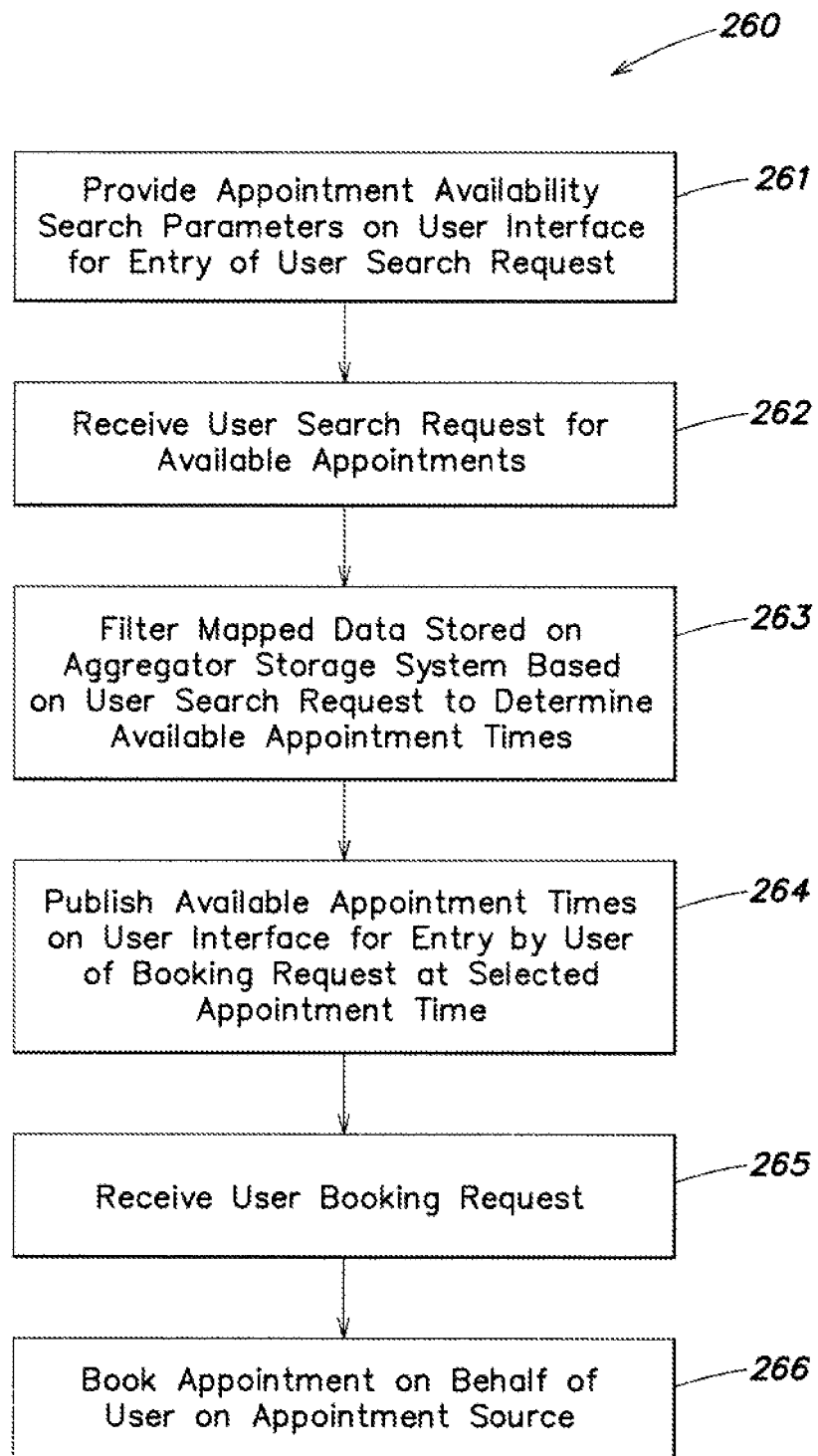
FIG. 11 is a flow chart illustrating one method of processing user searching and booking requests according to one embodiment of the invention.

FIG. 11 illustrates another method embodiment 260 which includes steps of publishing the stored availability data for searching by the user and booking of an appointment on behalf of a user (patient). In a first step 261, the availability data is published on a user interface and a user enters a search request correlating to one or more of the common formatted data parameters. In next step 262, the user search request for an available appointment is received. In next step 263, based on the user request, the stored (mapped) data is filtered to determine a set of available appointment times that best satisfy the search criteria. The next step 264, the set of available appointment times is published to the user display for entry by the user of a booking request at a selected available appointment time. In next step 265, the user booking request is received and in next step 266 an appointment is booked by the system on behalf of the user (patient) at the selected time with the respective source.

In accordance with the method described in FIG. 11, a patient can utilize the system 100 to search for provider availability data from multiple sources (previously collected and stored by the system 100) at a single location (user interface), select from the stored appointment times, and request to book a selected appointment. The system then books the appointment on behalf of the user with the respective source of the selected appointment. The user is no longer required to navigate different sites and has a much wider range of booking options for all of his or her healthcare needs.

Figure 12:
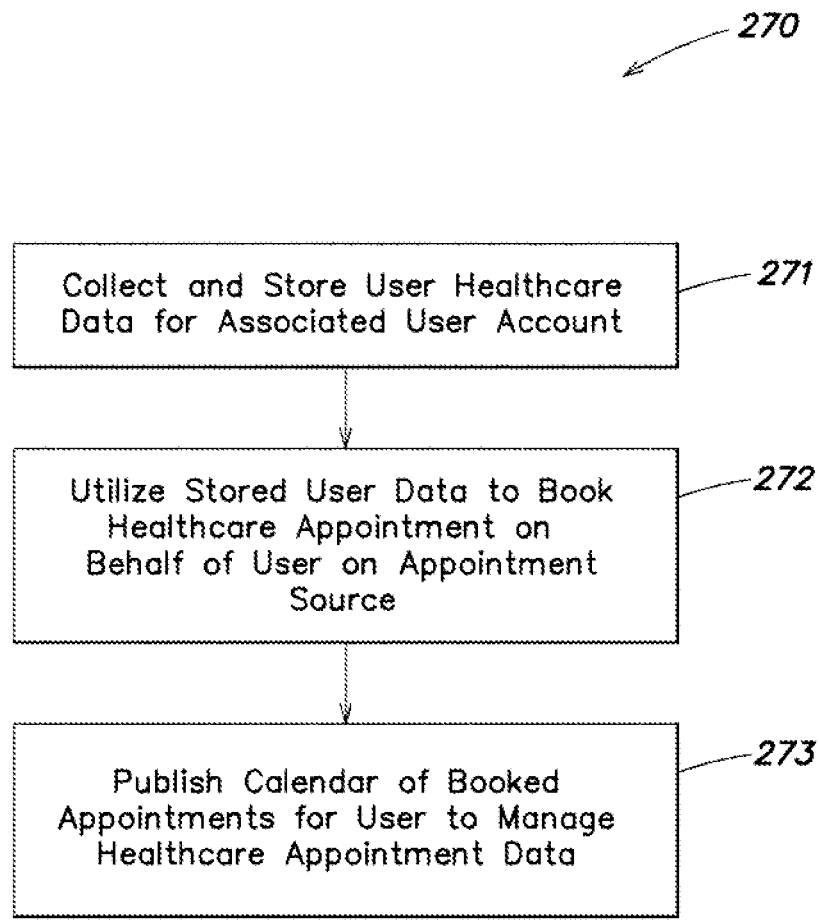
FIG. 12 is a flow chart illustrating one method of collecting and publishing a calendar of booked appointments for a user to manage healthcare appointment data.

FIG. 12 illustrates one method embodiment 270 for establishing a user account that enables the system to book appointments on behalf of the user (patient). In first step 271, the system collects and stores user healthcare data for an associated user account. Typically this is done via an interface (website or mobile application) wherein patient specific information is requested from the user to enable the system to access (on behalf of the patient) other sources (e.g., websites) of doctor availability via user access information (e.g., security information such as a user name and password), as well as other patient contact and healthcare data to facilitate both the booking and subsequent record keeping of booked appointments. In next step 272, the system books a healthcare appointment on behalf of the user and the booked appointment is stored as user healthcare data. In next step 273, the system publishes (e.g., via the user interface) a calendar of the user's booked appointment data enabling the user to manage his or her healthcare appointment data. The benefit is that all healthcare information can now be stored in a single location, by the system, and provided in a single interface (display) for the user to manage. If there is a change in any of the user healthcare data due to, for example, a change in employment, a change of insurance plan, or addition of a new provider, this data change can be input once by the user on the single interface and stored by the system as part of the user healthcare data for subsequent search ad booking requests, and for communication to the remote sources 105, 106. The user is no longer required to remember and enter the changed healthcare data across multiple platforms, namely the multiple sources of doctor availability data.

Figure 13:
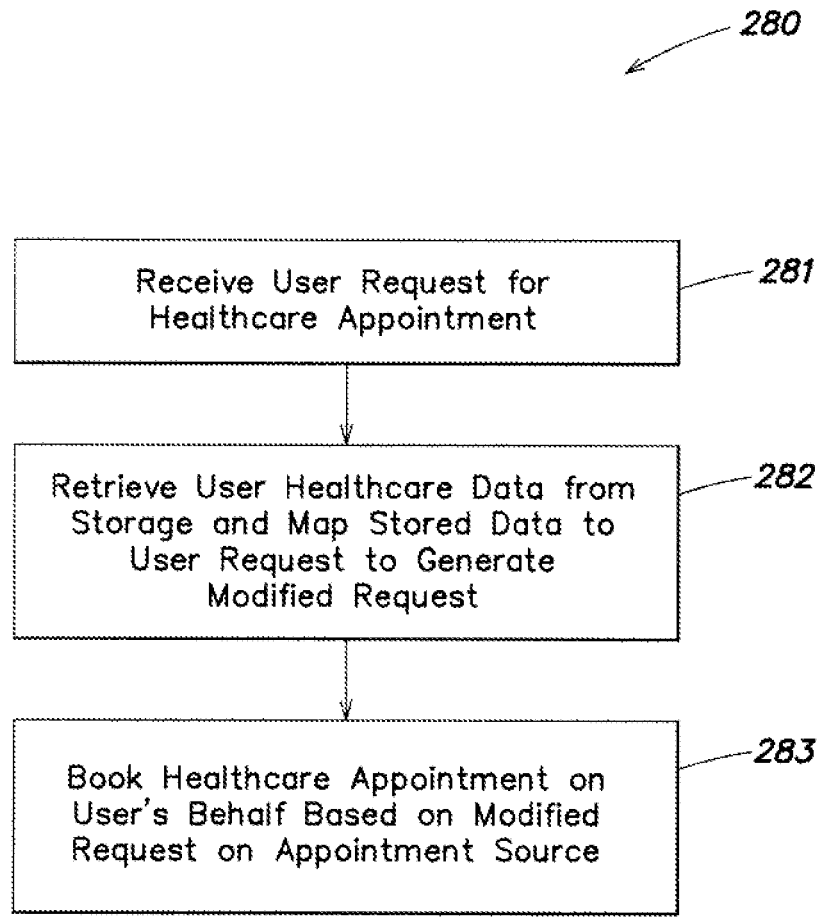
FIG. 13 is a flow chart illustrating one method of utilizing user account information for booking an appointment on the user's behalf.

FIG. 13 illustrates another method embodiment 280 of the invention. In this example, the system utilizes the stored user healthcare data to facilitate a booking request made by the user, without having to burden the user with requests for information that has already been stored. This is another benefit of maintaining (storing) updated user healthcare data at a single location. In the first step 281, a user request for a healthcare appointment is received. In next step 282, the user healthcare data is accessed from the storage system and mapped with the request to generate a modified request. In next step 283, the system then proceeds with booking a healthcare appointment on the user's behalf based on the modified request. For example, if the user healthcare data includes the user preference for early morning appointments, then that preference can be included with the system's booking request made to the source for booking on behalf of the user.

In another embodiment of the invention, various methods may be used for updating or refreshing the doctor availability data stored by the system. In one example, the system utilizes a sliding expiration date window for the stored healthcare availability data. As one example, an appointment further out in time, such as six months in the future, may be less likely to be booked by another entity and no longer available over a given expiration time period. In this case, the appointment is given a longer expiration time period before being deleted or refreshed. In another example, the expiration date may be determined based on a relative popularity rating (e.g., likelihood of being already booked by another entity at the time of the user's booking request). Such popularity may be based on the type of appointment (procedure), the office location, or the relative inventory of appointments available for a designated provider at a designated location and for a designated procedure.

i) User-Source Communication Management

In one embodiment of the invention, the system books healthcare appointments on behalf the user and also manages communications between the user and the source. These communications may be routed through the system to minimize the burden to the user, standardize the format of the communications, and allow the system to maintain healthcare user communication in the user's account.

Figure 14:
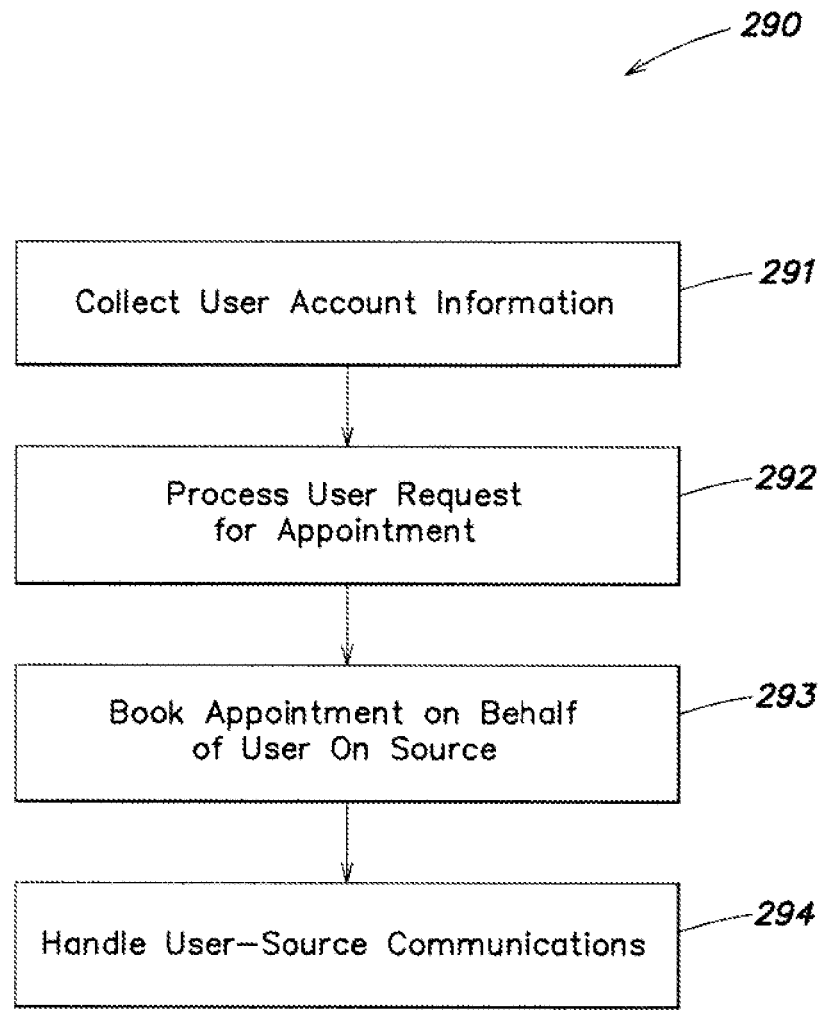
FIG. 14 is a flow chart illustrating one method of processing and booking appointments on behalf of a user on a remote source and handling user-source communications.

FIG. 14 illustrates one method embodiment 290 in which the system manages user-source communication. In a first deck, the system collects user account information 291, which as previously described, would typically include the user's encrypted credentials for accessing the remote site and also the user's electronic communication addresses (e.g., email and text message) by which the system and/or source may contact the user concerning a booking. In next step 292, a user's request for an appointment is processed (e.g., filtered to identify a suitable appointment time slot and source). In next step 293, the system books the user's selected appointment on behalf of the user on the source site, by accessing the source site as the user, utilizing the user's credentials. In next step 294, the system handles any or all user-source communications concerning that booking or otherwise with the source.

In one example, if a new user has no account on a particular source, the system may create an account on behalf of the user with a third party source for communications to and from the source. For example, the system can establish a system's email address used to create an account on behalf of the user, at the third party source. In one example, the system maps the system's email address to the user's email address (e.g., "jon.smith.thirdparty site #1@system.com" is mapped to jonsmith@gmail.com), enabling the system to receive and transmit communications between the user and the source.

In another example, the system maps a mobile phone number of the system with a mobile phone number of the user for intercepting or conveying text message communications between the user and the source.

j) Computer Environment

The previously described methods may be implemented in a suitable computing environment, e.g., in the context of computer-executable instructions that may run on one or more computers. For example, in a distributed computing environment certain tasks are performed by remote processing devices that are linked through a communications network, and program modules may be located in both local and remote memory storage devices. The communications network may include a global area network, e.g., the Internet, a local area network, a wide area network or other computer network. It will be appreciated that the network connections shown herein are exemplary and other means of establishing communications between the computers may be used.

A computer may include a processing unit, a system memory, and system bus, wherein the system bus couples the system components, including, but not limited to, the system memory and the processing unit. A computer may further include disk drives and interfaces to external components. A variety of computer-readable media can be accessed by the computer and includes both volatile and nonvolatile media, and removable and nonremovable media. A computer may include various user interface devices, including a display screen, touch screen, keyboard, or mouse.

Figure 15:
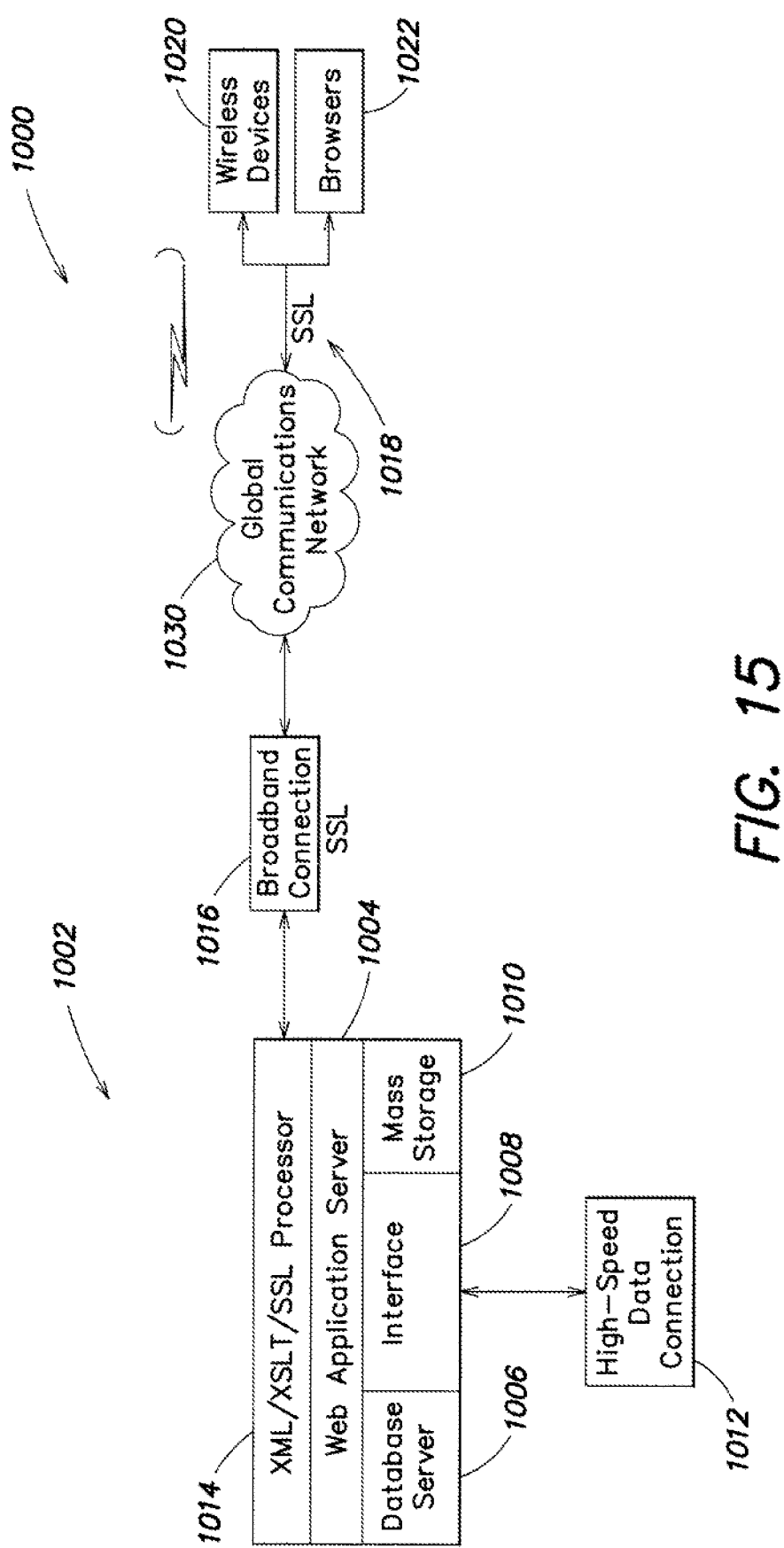
FIG. 15 is a schematic block diagram of a communications system that can be used in one embodiment of the invention.

Referring now to FIG. 15, there is illustrated a general system configuration 1000 for communications between the system, patients, providers and other third party availability sources. In one embodiment, a system platform 1002 hosts at least a data management tool, here a web application server 1004. The server 1004 provides a common layer to underlying services that include a database server 1006, a mass storage 1010, and an interface 1008, to a high-speed data connection 1012 (e.g., T1, DS3), to accommodate processing, storage and/or communications with remote locations and/or users (e.g., patients, practice groups) from virtually any accessible network node. Further, the platform 1002 can include a processor 1014 suitable for XML (extensible Mark-up Language), XSLT (XML Stylesheet Language, Transformations), and SSL (Secure Sockets Layer) processing. The processor 1014 can also access web based services utilizing SOAP (Simple Object Access Protocol). There is a high speed connection 1016 (e.g., broadband) that interfaces to the processor layer 1014 for multiple communication exchanges with remote users accessible on a global communications network 1030 (e.g., Internet). The remote users can access the platform 1002 via an SSL connection 1018 using portable wired/wireless devices 1020, or by way of the associated browsers 1022, or other applications.

In another aspect of the invention, a non-transitory computer-readable medium is provided, the medium including instructions for implementing the above-described information system and/or the computer implemented methods.

What has been described above includes examples of the present invention. It is, of course, not possible to describe every conceivable combination of components or methodologies for purposes of describing the present invention, but one of the ordinary skill in the art will recognize that further combinations and permutations of the present invention are possible. Accordingly, the present invention is intended to embrace all such alternations, modifications and variations that fall within the present disclosure and/or claims.

The invention claimed is:

1. A healthcare appointment availability information system, including a processor in electronic communication with a plurality of modules stored on a memory and executable by the processor, the modules comprising:
    an ingestion module configured to locate and retrieve healthcare appointment availability data from a plurality of disparate Internet-accessible sources comprising one or more of primary data sources and secondary data sources;
    a transformation module configured to select among ingested availability data retrieved from the disparate Internet-accessible sources and generate mapped data by mapping the selected ingested data to request parameters to identify an available healthcare provider appointment, wherein the selection is made by assigning a priority to each of the disparate Internet-accessible sources of ingested availability data based at least on primary or secondary data source type and selecting from among the ingested data based on the assigned priority;
    a storage module configured to store the ingested or mapped data;
    a filtering module for filtering the mapped data based on a user search or booking request to determine available appointment times that satisfy the user search or booking request;
    an interface module for generating an electronic interactive user interface for receiving user search and booking requests for an available provider appointment based on the request parameters and displaying the filtered appointment times based on the user requests; and
    a booking module for booking on behalf of the user a user selected available healthcare provider appointment with the respective source, utilizing user access information to access the respective Internet-accessible source as the user.

2. The availability information system of claim 1, wherein the transformation module is configured to map the selected ingested data to a time slot record for storage in the storage module, the time slot record including an associated provider, appointment location, start time, and end time.

3. The availability information system of claim 2, wherein the common time slot record further includes one or more of procedure type and patient type for the associated appointment.

4. The availability information system of claim 1, wherein the storage module is further configured to store user specific account information including a user identifier, a source identifier and user credentials to access the respective source as the user.

5. The availability information system of claim 4, wherein the user account information includes user specific preferences for healthcare providers, locations or appointment times, and the booking module is configured to utilize at least one of the user preferences for booking an available provider appointment on behalf of the user.

6. The availability information system of claim 1, wherein the system further includes a refresh module in electronic communication with the processor, the refresh module being configured to update the stored ingested or mapped data by triggering the ingestion module to periodically, at regular or variable time intervals, locate and retrieve the availability data from the sources.

7. The availability information system of claim 6, wherein the refresh module is configured to process one or more factors specific to the appointment time, provider, location or source, to determine the update time intervals.

8. The availability information system of claim 7, wherein the factors include one or more of:
    an amount of time to appointment;
    a popularity of appointment day or appointment time;
    a popularity of provider based on user selection;
    a rate of cancellations or rebookings by provider;
    a process time to retrieve availability data by source; and
    a search parameter for retrieving ingested data from source.

9. The availability information system of claim 1, wherein the ingested availability data includes at least one available time block; the transformation module is configured to extract the available time blocks from the ingested availability data and assign a priority which varies depending on the source of the extracted time block; and the transformation module is further configured to select among overlapping or conflicting extracted time blocks to generate a single unique time block record based on the priority.

10. The availability information system of claim 9, wherein the filtering module is configured to receive a user search request and filter the mapped data based on the user search request to generate a list of available appointment times from the time block records that satisfy the user search request.

11. The availability information system of claim 1, wherein the ingestion module is configured to locate and retrieve the availability data by searching, crawling or parsing websites that comprise the sources of the availability data or is configured to locate and retrieve the availability data via one or more application programming interfaces.

12. The availability information system of claim 1, wherein the sources comprise multiple websites, practice group servers, practice management servers, appointment scheduling servers, or provider servers.

13. The availability information system of claim 1, wherein the sources include aggregated sources of appointment availability data collected from multiple unaffiliated providers, and unaggregated sources of appointment availability data from one provider or one practice group.

14. The availability information system of claim 1, wherein the system further comprises a user-source communications module in electronic communication with the processor, the communications module configured for processing, on behalf of the user, user addressed electronic communications from the source.

15. The availability information system of claim 14, wherein the communications module maps an electronic address of the user and an electronic address of the system.

16. The availability information system of claim 1, wherein the ingestion module is configured to retrieve provider profile data from a source, compare the retrieved provider profile data to existing provider profile data stored on the storage module, and generate profile category specific requests to the source to retrieve category specific profile data.

17. A healthcare appointment availability information system, including a processor in electronic communication with a plurality of modules stored on a memory and executable by the processor, the modules comprising:
   an ingestion module configured to locate and retrieve healthcare appointment availability data from a plurality of disparate Internet-accessible sources comprising one or more of primary data sources and secondary data sources;
   a transformation module configured to select among ingested availability data for an associated provider retrieved from the disparate Internet-accessible sources and generate mapped data by mapping the selected ingested data to request parameters to identify an available healthcare provider appointment, wherein the selection is made by assigning a priority to each of the disparate Internet-accessible sources of ingested availability data for the associated provider based at least on primary or secondary data source type and selecting from among the ingested data based on the assigned priority;
   a storage module configured to store the ingested or mapped data;
   a filtering module for filtering the mapped data based on a user search or booking request to determine available appointment times that satisfy the user search or booking request;
   an interface module for generating an electronic interactive user interface for receiving user search and booking requests for an available provider appointment based on the request parameters and displaying the filtered appointment times based on the user requests; and
   a booking module for booking on behalf of the user a user selected available healthcare provider appointment with the respective source, utilizing user access information to access the respective Internet-accessible source as the user.

18. The availability information system of claim 17, wherein the storage module is further configured to store user-specific account information, wherein the user-specific information includes user-specific preferences for healthcare providers or appointment times, such that the user-specific information can be utilized by one or more of the filtering module and the booking module.

19. The availability information system of claim 18, wherein the user-specific account information includes user specific security information for accessing at least one appointment availability source as the user.

20. The availability information system of claim 17, wherein the system further comprises a refresh module in electronic communication with the processor, the refresh module being configured to update the stored ingested or mapped data by triggering the ingestion module to periodically, at regular or variable time intervals, locate and retrieve the availability data from the sources.

21. The availability information system of claim 17, wherein the disparate Internet-accessible sources include: practice management systems and appointment schedulers accessible via application programming interfaces, and websites.

22. The availability information system of claim 17, wherein the filtering module is further configured to determine an expiration time for the mapped data based on one or more of an amount of time prior to an appointment time, an appointment location, and an amount of available appointment times for a provider.

23. The availability information system of claim 17, wherein the ingestion module is configured to locate and retrieve availability data via web crawlers by initiating requests based on one or more of: provider location zip codes, provider accepted insurance plans, provider specialties or procedures, provider profile data for a designated provider, and available appointment times for a designated provider.

\* \* \* \* \*